US009629939B2

(12) United States Patent
Flynn et al.

(10) Patent No.: US 9,629,939 B2
(45) Date of Patent: Apr. 25, 2017

(54) COLLAGENOUS FOAM MATERIALS

(71) Applicant: Queen's University at Kingston, Kingston (CA)

(72) Inventors: Lauren E. Flynn, London (CA); Claire Yu, Kingston (CA)

(73) Assignee: Queen's University at Kingston, Kingston (CA)

( * ) Notice: Subject to any disclaimer, the term of this patent is extended or adjusted under 35 U.S.C. 154(b) by 0 days.

(21) Appl. No.: 14/403,396

(22) PCT Filed: May 16, 2013

(86) PCT No.: PCT/CA2013/000493
§ 371 (c)(1),
(2) Date: Nov. 24, 2014

(87) PCT Pub. No.: WO2013/173906
PCT Pub. Date: Nov. 28, 2013

(65) Prior Publication Data
US 2016/0051726 A1 Feb. 25, 2016

Related U.S. Application Data

(60) Provisional application No. 61/651,837, filed on May 25, 2012, provisional application No. 61/785,683, filed on Mar. 14, 2013.

(51) Int. Cl.
| | |
|---|---|
| *A61L 27/24* | (2006.01) |
| *A61L 27/26* | (2006.01) |
| *A61L 27/38* | (2006.01) |
| *A61L 27/56* | (2006.01) |
| *A61L 27/54* | (2006.01) |
| *B32B 5/32* | (2006.01) |
| *C08J 9/228* | (2006.01) |
| *C08L 89/06* | (2006.01) |
| *C08H 1/06* | (2006.01) |
| *A61L 27/36* | (2006.01) |
| *C08J 9/28* | (2006.01) |

(52) U.S. Cl.
CPC ............... *A61L 27/24* (2013.01); *A61L 27/26* (2013.01); *A61L 27/3633* (2013.01); *A61L 27/38* (2013.01); *A61L 27/54* (2013.01); *A61L 27/56* (2013.01); *B32B 5/32* (2013.01); *C08H 1/06* (2013.01); *C08J 9/228* (2013.01); *C08J 9/28* (2013.01); *C08L 89/06* (2013.01); *A61L 2300/64* (2013.01); *A61L 2430/34* (2013.01); *C08J 2201/0484* (2013.01); *C08J 2389/06* (2013.01)

(58) Field of Classification Search
None
See application file for complete search history.

(56) References Cited

U.S. PATENT DOCUMENTS

| | | | | | |
|---|---|---|---|---|---|
| 4,837,285 | A | * | 6/1989 | Berg ........................ | A61K 9/70 128/DIG. 8 |
| 4,863,856 | A | * | 9/1989 | Dean, Jr. .................. | C12N 1/00 435/174 |
| 2006/0159731 | A1 | * | 7/2006 | Shoshan ................. | A61K 38/39 424/443 |

FOREIGN PATENT DOCUMENTS

| | | | |
|---|---|---|---|
| WO | WO2010/088678 A2 | 8/2010 | |
| WO | WO2010088678 A2 * | 8/2010 | ............. A61L 27/36 |

OTHER PUBLICATIONS

Matsunaga et al. Molding cell beads for rapid construction of macroscopic 3D tissue architecture. Adv Mater. Mar. 25, 2011;23(12):H90-4.*
Ma et al. Thermal Cross-Linking for Biologically Degradable Materials Preliminary Report. ASAIO Journal 1996;42:M866-M871.*
Iwai et al. Biodegradable polymer with collagen microsponge serves as a new bioengineered cardiovascular prosthesis. J Thorac Cardiovasc Surg 2004;128:472-9.*
Tsai et al. Gel beads composed of collagen reconstituted in alginate. Biotechnology Techniques, vol. 12, No. 1, Jan. 1998, pp. 21-23.*
International Search Report dated Aug. 23, 2013 for International Application No. PCT/CA2013/000493 filed on May 16, 2013.
Written Opinion dated Aug. 23, 2013 for International Application No. PCT/CA2013/000493 filed on May 16, 2013.
Yu C., et al., "Porous decellularized adipose tissue foams for soft tissue regeneration" Biomaterials, 2013, 34(13), 3290-3302.

* cited by examiner

*Primary Examiner* — Satyanarayana R Gudibande
*Assistant Examiner* — Jia-Hai Lee
(74) *Attorney, Agent, or Firm* — Stephen J. Scribner

(57) ABSTRACT

Provided is a foam material, comprising a plurality of substantially collagenous beads, wherein the foam material is a bead foam, and wherein adjacent collagenous beads are fused together by a network of collagen fibers. Also provided are methods for preparation of foam materials comprising a plurality of substantially collagenous beads. The foam materials may be used in applications such as bioscaffolds for wound healing, soft tissue regeneration and augmentation, for localized cell delivery, or as cell culture substrates for research. The foam materials include natural collagen fibrils that provide a stable scaffold and enhance integration of the implanted scaffold and regeneration of cells and tissue.

22 Claims, 3 Drawing Sheets

COLLAGENOUS FOAM MATERIALS

FIELD

This invention relates to collagenous foam materials suitable for use in wound healing, soft tissue regeneration and augmentation, in vivo cell delivery, or as cell culture substrates for research.

BACKGROUND

In tissue regeneration strategies, 3-D scaffolds prepared from collagenous foams or sponges have been used to help restore damaged or missing tissues, or correct tissue voids. Natural collagenous foams are of interest because they provide the initial extracellular matrix (ECM) foundation for cells to attach and proliferate. A variety of scaffolding biomaterials derived from collagen are available. Porosity of these materials is critical since it allows for cellular penetration, nutrient and oxygen diffusion, and has been shown to direct the cell response in terms of viability, proliferation, migration, and differentiation by mediating 2-D cell spreading and 3-D intercellular contacts, depending on the pore size.

Foams have been fabricated with purified collagen from calf skin, bovine collagen, gelatin, porcine fetal collagen, and purified collagen type I (porcine, bovine, rat). Generally, the processes for fabricating these foams involve solubilization of the collagenous material followed by drying to yield a porous structure. In the solubilization step, a dilute acid is often used with or without an additional enzymatic digestion to create a collagen suspension that would otherwise be insoluble in aqueous solution. The solution is then poured into a preformed mould where it is frozen and freeze-dried, or in some cases immersed in ethanol and critically point dried. This general approach is dependent on ice crystal formation as a porogen and can be easily controlled by varying the collagen solution concentration and freezing temperatures. Other variations on this method include solvent-casting, emulsion freeze drying, particulate leaching, and gas foaming.

In vivo studies have shown that foams fabricated in this fashion exhibit poor cellular infiltration with only a few cells migrating as far as 500 µm into the foams, alone with an observable monolayer growth of up to approximately 100 µm. A major challenge arises in poor diffusion of nutrients and oxygen into the interior, as the surface pores are blocked by the expansion of cells over time. As a result, several groups have addressed the need for a long ranging channeling microarchitecture construct. In particular, the use of solid free form (SFF) technology is gaining popularity in which 3-D printers are used to fabricate custom casting moulds designed using computer-aided design (CAD) software. For example, using available layer-by-layer 3-D printing techniques, complex channels larger than 100 µm can be achieved with high degree of control and resolution. However, drawbacks include the inherent difficulty in removing residual powders as well as toxic solvents and binders in the complex channels, poor mechanical strength of the constructs, and in some cases high temperatures are used which can degrade biological components. In addition, the use of sacrificial moulds has also been explored whereby moulds constructed using SFF are filled with a collagen solution. Upon solidifying the collagen solution, the mould is degraded thermally or chemically, but once again, residual moulding materials and extreme techniques may prove unfavourable to the final product.

An alternative approach in forming porous foams uses an ice particulate template method whereby pore size can be made larger at the surface than the interior. This strategy depends solely on ice crystal formation to control the degree of porosity. Ice particles are formed by spraying water onto a plate and frozen at various temperatures to achieve different sized spheres. The ice particulates are embossed onto a silicone frame into which a solution of supercooled collagen is poured. Following this, the entire construct is frozen and lyophilized. Since many of these foams have poor mechanical strength upon fabrication, crosslinking agents such as glutaraldehyde, EDC/NHS, and genipin have been used. However, crosslinking presents cytotoxicity risks and may affect the porosity of the foam, as it is difficult to control the degree of crosslinking desired.

Commercially-available foams approved for clinical use include Colla Plug®, Colla Cote®, and Colla Tape® (Zimmer Dental Inc., U.S.A.) a family of resorbable bovine collagen type I plugs, foams, and tapes. In addition, Gelfix® (Abdi ibrahim, Turkey), a foam prepared from lyophilized collagen, and GelFoam® (Pfizer), a sterile sponge prepared from porcine skin gelatin USP granules, are also used in surgical procedures. Although such materials are easily accessible and acceptable for human use, these products may pose xenogenic risks.

Clearly there is a need for a foam material without the above drawbacks for use in wound healing, soft tissue regeneration and augmentation applications.

SUMMARY

One aspect of the invention provides a foam material, comprising a plurality of substantially collagenous beads. The foam material may be a bead foam. The adjacent collagenous beads may be fused together by a network of collagen fibres. The substantially collagenous beads may comprise collagen fibres and have primary porosity including pores between individual fibres and/or pores between groups of fibres. The foam material may have secondary porosity including pores between individual beads and/or pores between groups of beads. In one embodiment, a pore size of the secondary porosity is greater than a pore size of the primary porosity.

The foam material may have a selected structure and/or a selected shape. The structure may comprise one or more layers of substantially collagenous beads; or the foam material may have a selected shape and the structure may comprise one or more layers of substantially collagenous beads. The foam material may comprise two or more layers of bead foam; and one or more of cells, cell-seeded sponge foam, cell-seeded bead foam, and cell-seeded substantially collagenous beads. In one embodiment the selected shape is determined by a mould.

The beads may have a spherical, substantially spherical, rod-like, or random shape, or a combination of two or more such shapes. The collagenous beads may comprise collagen fibres derived from an extracellular matrix (ECM) obtained from animal tissue. The ECM may be obtained from human tissue.

The beads and/or the foam material may include at least one chemical/biological agent. In various embodiments the at least one chemical/biological agent is a cell, DNA, RNA, a protein, an antibody or other binding protein, a drug, a growth factor, a hormone, an analgesic, an anaesthetic, or a combination thereof. The beads and/or the foam material may include at least one additive, wherein the additive comprises a natural polymer, a biodegradable synthetic polymer, a non-biodegradable synthetic polymer, or a combination thereof.

Another aspect of the invention provides an implantable medical structure comprising a foam material as described herein. In one embodiment the implantable medical structure is a scaffold. The implantable medical structure may be used in wound repair or soft tissue regeneration and augmentation. The foam material may be used as a cell culture substrate.

Another aspect of the invention provides a method for preparing a foam material, comprising: freezing a plurality of substantially collagenous beads at a selected temperature; and subjecting the beads to freeze-drying; wherein a first foam material having pores between individual beads and/or pores between groups of beads is prepared. The substantially collagenous beads may comprise collagen fibres derived from an extracellular matrix (ECM) obtained from animal tissue. The ECM may be obtained from human tissue.

The method may include freezing the plurality of substantially collagenous beads in a mould. The method may include forming a foam layer over the first foam material by: (i) covering the first foam material with a second plurality of substantially collagenous beads; and (ii) subjecting the beads to freezing and freeze-drying; and optionally repeating (i) and (ii) two or more times; wherein a layered foam material is prepared. The beads may have a spherical, substantially spherical, rod-like, or random shape, or a combination of two or more such shapes. The beads of the first foam material or of at least one layer may have a different shape or combination of shapes than the beads of at least one other layer. The method may include forming the first foam material or at least one layer using a mould. The method may comprise (a) preparing a second bead foam material; (b) disposing one or more of one or more of cells, cell-seeded sponge foam, cell-seeded bead foam, and cell-seeded substantially collagenous beads between the first foam material and the second foam material; optionally repeating (a) and (b) two or more times; wherein the cells aggregate the foam materials together to form a layered foam material.

The method may include combining at least one chemical/biological agent with the beads. In various embodiments the at least one chemical/biological agent is a cell, DNA, RNA, protein, an antibody or other binding protein, a drug, a growth factor, a hormone, an analgesic, or an anaesthetic, or a combination thereof. The method may include combining at least one chemical/biological agent with the beads of at least one layer. The method may include combining at least one additive with beads and/or the foam material, wherein the additive comprises a natural polymer, a biodegradable synthetic polymer, a non-biodegradable synthetic polymer, or a combination thereof.

In the above aspects, the collagenous beads may include a combination of fibrous and network type collagens. In certain embodiments the collagenous beads include type IV collagen. In some embodiments the collagenous beads may include one or more of collagens type I to III, V, and VI. In some embodiments the collagenous beads may include elastin and/or elastic fibres. In some embodiments the collagenous beads may include laminin, fibronectin, or both. In some embodiments the collagenous beads may include hyaluronan, chondroitin sulphate, or both. In some embodiments the collagenous beads may include one or more proteoglycan, glycoprotein, or glycosaminoglycan, or any combination thereof.

BRIEF DESCRIPTION OF THE DRAWINGS

For a better understanding of the invention, and to show more clearly how it may be carried into effect, embodiments will be described, by way of example, with reference to the drawings, wherein.

DETAILED DESCRIPTION OF EMBODIMENTS

According to one aspect of the invention there are provided porous collagenous foams derived from the extracellular matrix (ECM) that can be used as bioscaffolds for wound healing, soft tissue regeneration and augmentation, for localized cell delivery, or as cell culture substrates for research. The foams are produced from solubilized collagens isolated from cells or tissues (human or other animal), through a process including controlled freezing and lyophilization. The process preserves the complex extracellular matrix (ECM) of the tissue source, including the natural collagen fibrils that are necessary for producing a stable scaffold and that ultimately lead to integration of the implanted scaffold and regeneration of to cells and tissue.

The collagens may include a combination of fibrous and network type collagens. For example, in certain embodiments the collagens may include type IV collagen. In other embodiments the collagens may include one or more of collagens type I to III, V, and VI. Other components may also be present with any of the above collagens. For example, in some embodiments elastin and/or elastic fibres may be present. As another example, in some embodiments laminin, fibronectin, or both may be present. As another example, in some embodiments hyaluronan, chondroitin sulphate, or both may be present. As a further example, in some embodiments one or more proteoglycan, glycoprotein, or glycosaminoglycan, or any combination thereof, may be present.

Figure 1:
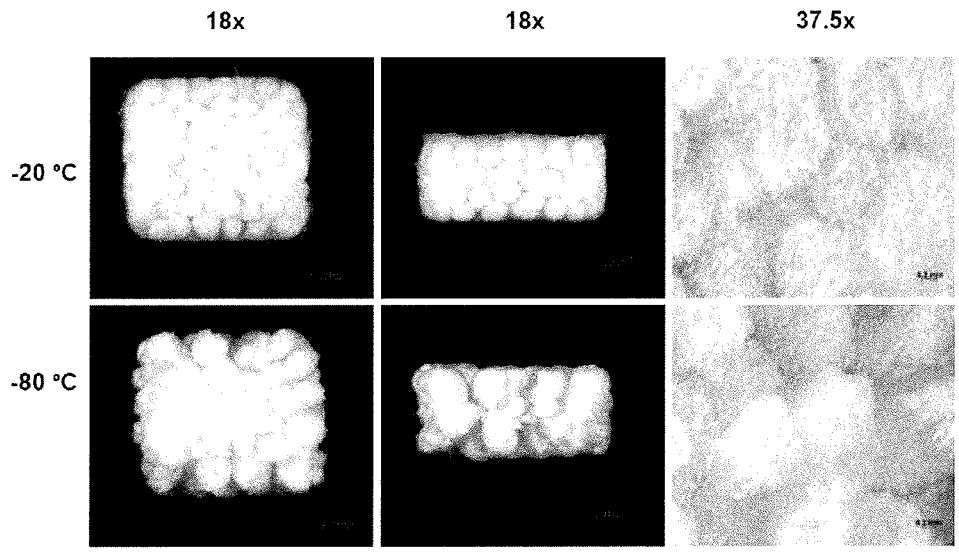
FIG. 1 shows photomicrographs of bead foams prepared from small beads (approximately 1-2 mm diameter) made from decellularized adipose tissue (DAT) as the collagen source, at 50 mg/mL concentration, with freezing temperatures of −20° C. and −80° C.
Figure 2:
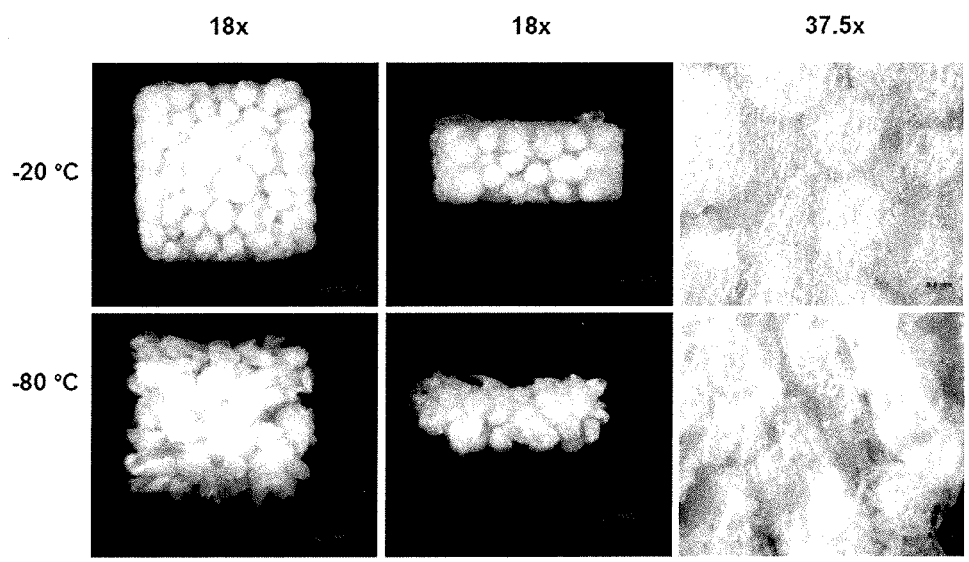
FIG. 2 shows photomicrographs of bead foams prepared from small beads (approximately 1-2 mm diameter) made from DAT as the collagen source, at 25 mg/mL concentration, with freezing temperatures of −20° C. and −80° C.
Figure 3:
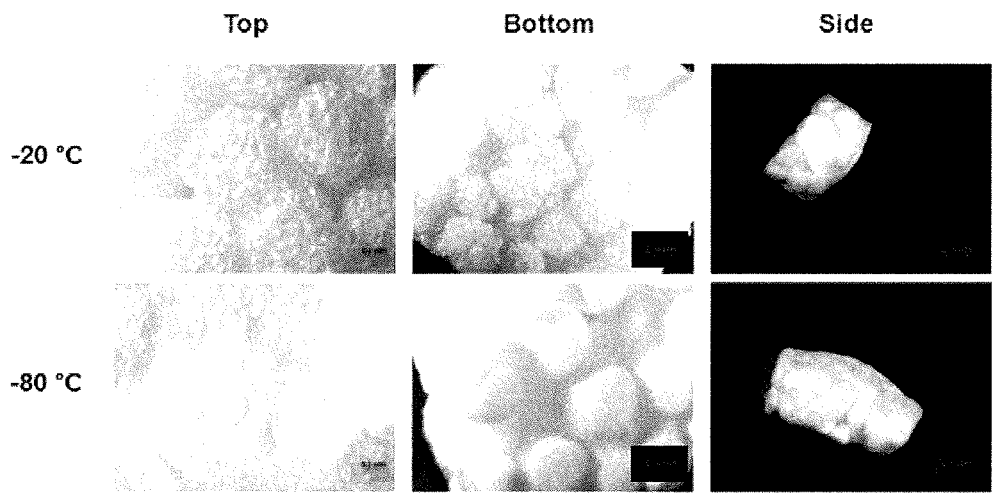
FIG. 3 shows photomicrographs of bead foams prepared from large beads (approximately 2-3 mm diameter) made from DAT as the collagen source, at 50 mg/mL concentration, with freezing temperatures of −20° C. and −80° C.
Figure 4:
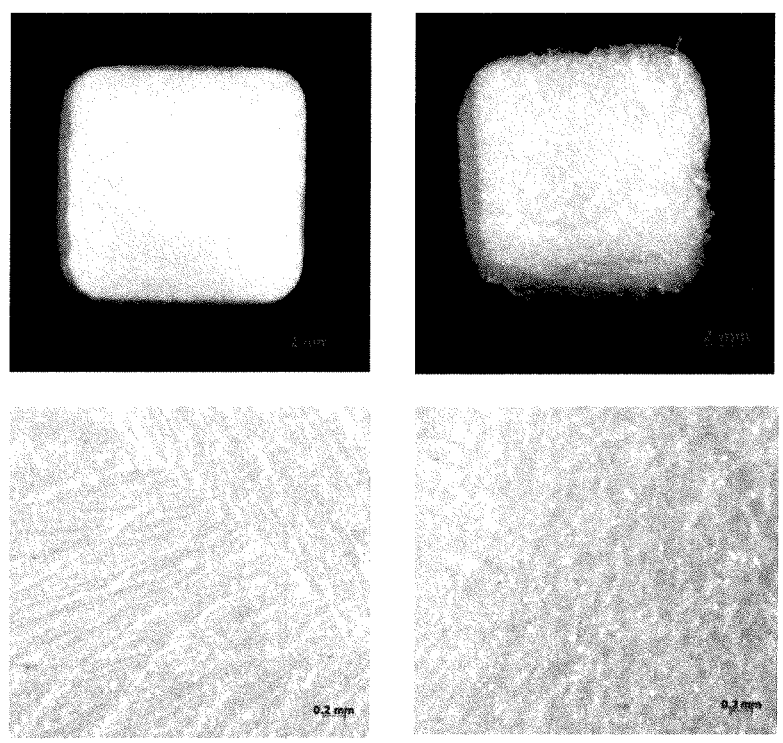
FIG. 4 shows photomicrographs of sponge foams prepared from DAT as the collagen source. Images on the left show a DAT sponge foam fabricated at 100 mg/mL concentration with a freezing temperature of −80° C. Images on the right show a DAT sponge foam fabricated at 50 mg/mL concentration with a freezing temperature of −20° C.
Figures 5A, 5B, 5C:
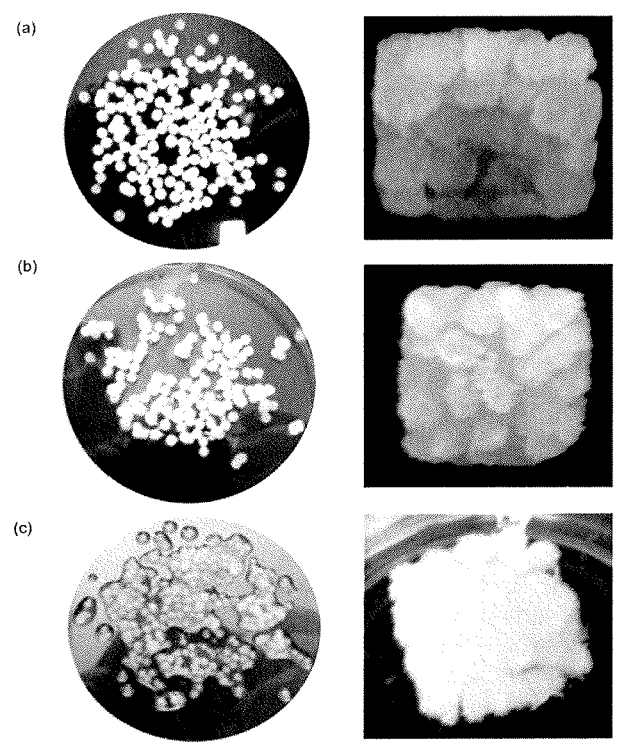
FIGS. 5($a$)-5($c$) show photomicrographs of bead foams prepared from decellularized porcine cardiac tissue as the collagen source, at 50 mg/mL concentration, with a freezing temperature of −80° C. Images shown depict hydrated decellularized cardiac bead foams made from (a) beads with an average diameter of 330 microns, (b) beads with an average diameter of 290 microns, and (c) beads with an average diameter of 200 microns.

Foams as described herein may comprise beads (e.g., FIGS. 1-3, 5($a$)-5($c$)) or be sponge-like (i.e., microporous) (e.g., FIG. 4), and may be produced in layers and/or in one or more moulds so as to have a desired shape and 3-D volume. Sponge-like foams as described herein have as porosity which is substantially uniform throughout the foam, referred to herein as primary porosity. Primary porosity results from spaces between collagen fibres and/or groups of collagen fibres. The porosity can be altered by adjusting process parameters such as freezing temperature and collagen concentration.

For the bead foams, the beads may be of any shape, or combination of shapes, such as spherical, spheroidal, rod-like, or random shape. The beads may be produced from any collagenous (fibrillar protein) source, using techniques known in the art, such as, for example, electrospray. Alternatively, a sheet or 3-D scaffold may be prepared and then mechanically processed to obtain smaller beads, and/or beads of a selected size and/or shape. The beads have primary porosity which results from spaces between collagen fibres and/or groups of collagen fibres. The pore size of the primary porosity may be in the range of, for example, 10-200 µm, or 10-100 µm, or 50-100 µm diameter. However, other pore sizes and ranges may be created, as the primary porosity may be altered by adjusting process parameters during production of the beads.

Bead foams produced by fusion of beads as described herein have primary porosity, as described above, and secondary porosity that results from spaces between beads or groups of beads, which may include interconnecting channels between individual beads and/or groups of beads. Secondary porosity of the bead foam may be adjusted by varying one or more of the size, shape, and packing density of the beads that are subsequently packed together and fused, and/or one or more process parameters such as freezing temperature and duration. For example, spherical and/or non-spherical bead geometries (e.g., rods, spheroids, random particles) and/or varying size distributions may be used to tailor the packing density, porosity, and scaffold morphology of the bead foams. As one example, using small substantially spherical beads and a high packing density, the secondary porosity may be as small as 100 µm, or smaller. However, using larger beads and/or a lower packing density results in a bead foam with larger secondary porosity, such, for example, 200-1000 µm, or 300-700 µm, or 400-500 µm diameter. Further, using a variety of bead sizes, shapes, and/or packing densities, a bead foam with secondary porosity including regions of different sizes of pores may be produced. Furthermore, conventional techniques to increase foam porosity (e.g., porogens, special moulds) may also be applied using the beads rather than the solubilized collagen solution, to further tune the overall scaffold porosity. In some embodiments pore size of the secondary porosity is generally larger than pore size of the primary porosity. The combined primary and secondary porosity of bead foams provides a much larger surface area to support the cellular infiltration and diffusion necessary for large constructs.

Foams as described herein may include at least one chemical/biological agent. Such an agent or combination of agents may conveniently be incorporated into the foam during fabrication, or may be added to the foam after fabrication. A chemical/biological agent may be, but is not limited to, a cell, DNA, RNA, a protein, an antibody or other binding protein, a drug, as growth factor, a hormone, an analgesic, an anaesthetic, or a combination thereof. The antibody may be polyclonal or monoclonal.

In some embodiments, substantially collagenous foam materials are provided that include one or more additive. The additive may be included during preparation of beads from collagenous material, or it may be included with beads during preparation of foam material, or both. Inclusion of one or more additive may provide the ability to tune one or more properties of the foam material. For example, an additive may be used to make beads and bead foam materials more rigid and/or more stable, such as may be required in certain applications, for example, long-term culture.

The additive may be one or more natural polymer or one or more synthetic polymer, or combinations thereof. Various embodiments may include biodegradable polymers, or non-biodegradable polymers. The selection of a biodegradable polymer or non-biodegradable polymer may be related to a specific application. For example, biodegradable polymers may be included in embodiments that are implanted into a subject's body, whereas non-biodegradable polymers may be included in embodiments that are used in, e.g., cell culture applications.

Examples of natural polymers include, but are not limited to, collagen from multiple decellularized tissue sources (e.g., demineralized bone matrix, decellularized bone, decellularized blood vessels, decellularized cartilage, decellularized placenta, decellularized heart valves, decellularized ligament, decellularized dermis, decellularized myocardium, decellularized pericardium, decellularized smooth muscle, decellularized intestine, decellularized mucosa, decellularized nerve), gelatin, hyaluronan, chondroitin sulphate, heparan sulphate, chitosan, alginate, silk, elastin, or fibrin, and derivatives thereof.

Examples of biodegradable synthetic polymers include, but are not limited to, polycaprolactone (PCL), polyester, polyurethane, poly(ethylene glycol) (PEG), polylactic acid/polylactide (PLA), polyglycolic acid/polyglycolide (PGA), and polylactic co-glycolic acid (PLGA).

Examples of non-biodegradable synthetic polymers include, but are not limited to, polytetrafluoroethylene (PTFE), polystyrene, polyvinyl chloride (PVC), polyethylene terephthalate (PET).

As noted above, an additive may be used to make beads and bead foam materials more rigid and/or more stable, such as may be required in long-term culture. For example, a polystyrene bead may be coated with solubilized collagen from DAT or another tissue source, and the resulting coated beads used to prepare a bead foam. Further, such a foam material may be seeded with cells, wherein the collagen would be remodelled as the cells infiltrated, but the polystyrene beads would at least partially retain the overall structure because they would remain unchanged.

The amount of additive used, relative to e.g., the amount of collagen, may depend on the specific additive being used, what form it is in, and the intended application of the resulting beads and bead foam. However, in general the bead foam material comprises sufficient collagen to facilitate the formation of a foam fused by interconnections between the network of collagen fibers in adjacent beads.

One embodiment relates to as layered bead foam, including two or more layers of bead foams prepared with the same or different pore sizes. A layered bead foam may comprise an embedded network which may have different collagen types and pore sizes in the various layers, prepared, for example, by using multiple bead shapes and sizes to control the packing density in the different layers. For example, a first layer may have a first selected bead geometry and/or distribution, and a second layer may have a second selected bead geometry and/or distribution different from the first layer. Further, different structures may be created and then embedded into further layers, optionally using moulds to prepare one or more of the layers. For example, the layers may be prepared using a series of moulds of varying (e.g., increasing) size, or shape, etc. Such a bead foam would have utility in, for example, a scaffold, allowing tuning of degradation properties of the scaffold as healing/tissue regeneration progresses. Further, such a bead foam conveniently allows for one or more chemical/biological agents, as mentioned above, to be differentially incorporated therein, in one or more of the various layers. For example, a chemoattractive factor may be incorporated within the core region (i.e., a first layer), creating a gradient throughout the entire scaffold that might promote cell infiltration. As another example, an angiogenic factor may be incorporated into pores or channels between beads of a layer that is then embedded inside another layer, to guide vascularization.

In another embodiment, a layered bead foam comprising two or more layers, such as described above, may be prepared by seeding one or more bead foams with cells. The bead foams are then placed together, whereupon the cells provide matrix that adheres to and aggregates the bead foam layers together. Preparation may include culturing the cells before and/or after placing the bead foams together, wherein culturing enhances fusion of the bead foams by the cells. Such cell-seeding may allow preparation of a layered bead foam without freeze-thaw and lyophilization steps to achieve fusion of the layers.

In another embodiment, a layered bead foam comprising two or more layers may be prepared from one or more cell-seeded bead foam layers as described above and one or more unseeded bead foam layers. For example, a layered bead foam may comprise alternating layers of cell-seeded and unseeded bead foams. According to this embodiment the cells in the cell-seeded bead foam layers provide matrix that adheres to and aggregates the cell-seeded and unseeded layers together. Such cell-seeding may allow preparation of a stacked layered bead foam without freeze-thaw and lyophilization steps to achieve fusion of the layers.

In another embodiment, a layered bead foam comprising two or more layers may be prepared by disposing cell-seeded beads between the layers, and culturing the cells. The bead foam layers may be unseeded, or one or more layers may be cell-seeded. As in the previous embodiments, the cells provide matrix that adheres to and aggregates the beads and the layers together, and may allow preparation of a layered bead foams without freeze-thaw and lyophilization steps to achieve fusion of the layers.

In the above embodiments, one or more layers may alternatively be a sponge foam as described herein, either as a cell-seeded layer or as an unseeded layer.

In the above embodiments, the cells may comprise any cell that can produce ECM, examples of which include, but are not limited to, adipose-derived stem cells, bone marrow derived mesenchymal stem cells, embryonic stem cells, induced pluripotent stem cells, adipocytes, adipoblasts, pre-adipocytes, cardiomyocytes, cardiac fibroblasts, cardiac stem cells, chondrocytes or de-differentiated chondrocytes, osteocytes, myocytes, endothelial cells, endothelial progenitor cells, epithelial cells, fibroblasts, hematopoietic stem cells, pericytes, neurons, neural stem cells, neural crest cells, and glial cells, and combinations thereof. In some embodiments cell seeding may be tissue-specific. For example, cardiac fibroblasts and/or cardiomyocytes may be seeded on decellularized cardiac beads or bead foam.

Use of a mould as described herein allows control over the distribution of beads during the preparation of the foam. However, use of a mould is not essential. For example, as viscous collagen solution may be extruded or sprayed in a controlled fashion (e.g., similar to direct writing) onto a cold surface, for the initial freezing step, and then additional layers may be built up in a controlled way.

Imaging data and 3-D printing may be used to generate patient-specific moulds, or a variety of off-the-shelf formats could be prepared. The size and shape of foams produced as described herein closely matches the 3-D geometry of the moulds used for the scaffold synthesis. The foams are soft and flexible, but can be handled with forceps and sutured. The foams may be stored stably in a dried format (e.g., as an off-the-shelf biomaterial) and rehydrated when needed. Preliminary characterization studies on both types of foams described herein show they are stable when rehydrated in aqueous solution without significant shrinkage upon cell culturing. Thus, crosslinking of the collagen is not required for structural integrity of the foams. However, in some embodiments crosslinking may be desirable, for example, to change mechanical properties of the foam and/or to tailor the mechanical properties for a given application. Nevertheless, the ability to avoid crosslinking is advantageous insofar as crosslinking agents may present cytotoxicity risks and reduce the scaffold porosity.

Foams as described herein may be produced from any fibrous collagenous source, decellularized tissue, or ECM, for use in tissue-specific cell culture or regenerative approaches. For example, human adipose tissue is a convenient source of collagen, which may be decellularized (if required) according to an efficient protocol that we have developed (see co-pending U.S. application Ser. No. 12/971,531). The protocol has been optimized such that the product yields are maximized, processing time is minimized, and low cost materials are used, and is ideally suited for scaling-up.

Decellularized adipose tissue (DAT) is particularly attractive for use in a foam because the ECM material is rich in basement membrane, which is important in wound healing and cell survival, proliferation, and differentiation. The inventors also have evidence that foams prepared from DAT may be adipo-inductive, similar to that observed for intact DAT scaffolds and DAT microcarriers.

Others have proposed collagen-based foam constructs using purified animal-derived collagen or gelatin (denatured collagen), such as calf-skin gelatin and porcine fetal collagen, which present xenogenic risks. Using human sources of ECM as described herein not only circumvents these risks but also has the potential for improved implant response since ECM components are crucial to promoting cell signaling processes, and the foam mimics native tissues more closely. Nevertheless, foams as described herein may be prepared from any ECM source, including ECM from other species. For example, in other illustrative embodiments herein, foams have been synthesized from porcine decellularized myocardium.

Foams as described herein are natural reconstructive materials that may be used as volume fillers (either patient-specific or off-the-shelf) in procedures such as, for example, but not limited to, tumour resection, traumatic injury, or congenital birth defects. The foams may also be prepared as sheets for the treatment of, for example, but not limited to, burns, wounds, ulcers, oral mucosa damage, or large skin biopsies, or made into hollow tubes to provide scaffolding for cultivating artificial arteries or for use as nerve guidance channels.

Further, foams as described herein may be prepared as sheets or plugs for use in general surgery, such as, for example, bowel or fistula repair, bladder and urological repair, abdominal wall repair, vaginal repair, and filling voids post biopsy, or as sheets for corneal reconstruction, or as structures for orthopaedic applications requiring soft tissue augmentation. The foams may be used to deliver cells for applications in myocardial or cardiovascular regeneration, liver regeneration, kidney regeneration, or pancreatic islet cell transplantation. Another application is as a soft tissue filler material in cosmetic surgeries for restoring minor facial defects. For instance, a foam as described herein may be used as an implantable material for lip augmentation or correcting wrinkles and scars.

Preparation of foams as described herein can provide natural scaffolds from any collagenous (fibrillar protein) source, enabling tissue- or cell-specific approaches with foams for use in cell culture and/or tissue augmentation and regeneration. Obtaining collagen using enzymatic digestion conditions results in highly preserved collagen fibrils, facilitating stable foam formation without necessitating chemical crosslinking. However, crosslinking may be used if needed. Use of human ECM allows for the potential use as autologous or allogenic scaffolds, eliminating concerns with xenogenic disease transmission or immunogenicity.

Methods described herein may be used to develop foams from other collagen sources for tissue-specific applications. For example, cardiac extracellular matrix could be used for the proliferation of cardiomyocytes, bone matrix for osteoblasts, or decellularized dermis for dermal fibroblasts. Tissue-specific approaches are preferred, as the ECM composition profoundly impacts cellular behaviour, including proliferation, migration, morphology, and differentiation.

The foam materials and methods described herein are applicable to aligned fiber scaffold materials. For example, collagen-based fibers may be prepared and packed together in either an aligned (oriented) or random fashion, optionally using a mould, using the methods described herein.

The invention is further described by way of the following non-limiting examples.

EXAMPLES

Preparation of Foams from Collagenous Decellularized Extracellular Matrix

Example 1

Solubilization of Decellularized Extracellular Matrix Tissue

The solubilization of decellularized extracellular matrix tissue was adapted from methods established by Stevens [1]
1. Wash the decellularized tissue repeatedly in 5% (w/v) NaCl followed by washing in deionized water. Remove any excess liquid in between each washing regime.
2. Re-suspend in 0.22 M $NaH_2PO_4$ and adjust pH to 5.4. Add 0.3% (w/w) α-amylase to the tissue and agitate continuously at 18° C. (room temperature) for 72 h.
3. After digestion, wash the suspension repeatedly with 5% (w/v) NaCl followed by water and homogenize in a large volume of 0.2 M acetic acid. Allow the acetic acid mixture to agitate at 37° C. continuously for 48 h with periodic homogenization.
4. Centrifuge the solution at 1,200×g for 5 min and collect the collagen supernatant. Re-extract the insolubilized residue once more with acetic acid and pool together the supernatants.

Example 2

Preparation of Sponge Foams

Porosity of the foams may be controlled by varying concentrations (e.g., 100%, 50%, 25% solutions) of the solubilized collagen and freezing temperatures (e.g., −20° C., −80° C.) employed prior to lyophilization (i.e., freeze-drying).
1. Prepared solubilized collagen was carefully pipetted into preformed moulds and frozen at the desired temperature until completely solid.
2. The frozen constructs were then placed into a freeze-drier overnight.

Example 3

Preparation of Bead Foams

Beads used in preparation of these foams were made using a method adapted from Kim et al. [2]. Primary porosity may be controlled by varying the concentration and freezing temperatures. Secondary porosity may be controlled by varying the size of beads fabricated.
1. Beads were prepared by electrospraying the solubilized collagen through a 25 G needle directly into liquid nitrogen. Size of the beads may be controlled by varying the needle gauge and voltage applied.
2. The heads were collected and allowed to completely thaw at room temperature.
3. The thawed beads were carefully placed into a preformed mould and frozen at the desired temperature until completely solid.
4. The frozen bead constructs were placed into a freeze-drier overnight. (The constructs may be removed from the mould prior to freeze-drying, or subjected freeze-drying while in the mould.)

The contents of all references, pending patent applications, and published patents cited throughout this application are hereby expressly incorporated by reference.

Equivalents

Those skilled in the art will recognize or be able to ascertain variants of the embodiments described herein. Such variants are within the scope of the invention and are covered by the appended claims.

REFERENCES

1. Stevens, F. S., The Nishihara technique for the solubilization of collagen. Application to the preparation of soluble collagens from normal and rheumatoid connective tissue. *Ann. Rheum. Dis.* 1964, 23:300-301.
2, Kim, M. Y., Lee, J., Chitosan fibrous 3D networks prepared by freeze drying. *Carb. Poly.* 2011, 84:1329-1336.

The invention claimed is:
1. A foam material, comprising:
a plurality of collagenous beads;
wherein adjacent collagenous beads are fused together by collagen fibers;
wherein the foam material comprising a plurality of collagenous beads retains a 3-D shape.
2. The foam material of claim 1, wherein:
the collagenous beads are porous.
3. The foam material of claim 2, wherein:
the foam material has channels between individual collagenous beads and/or between groups of collagenous beads.
4. The foam material of claim 1, wherein:
the foam material has a structure comprising one or more layers of collagenous beads; or
wherein the foam material has a selected shape and a structure comprising one or more layers of collagenous beads.

5. The foam material of claim 1, wherein the structure comprises:
two or more layers of the foam material; and
cells and/or cell-seeded beads and/or cell-seeded foam disposed between the two or more layers of the foam material.

6. The foam material of claim 1, wherein:
the collagenous beads have a spherical or rod-like shape, or a combination of two or more such shapes.

7. The foam material of claim 1, including at least one chemical/biological agent, at least one additive, or at least one chemical/biological agent and at least one additive.

8. The foam material of claim 7, wherein:
the at least one chemical/biological agent is a cell, DNA, RNA, a protein, an antibody or other binding protein, a drug, a growth factor, a hormone, an analgesic, an anaesthetic, or a combination thereof.

9. The foam material of claim 7, wherein:
the at least one additive is a natural polymer, a biodegradable synthetic polymer, a non-biodegradable synthetic polymer, or a combination thereof.

10. An implantable medical structure comprising the foam material of claim 1.

11. The implantable medical structure of claim 10, wherein the structure is a scaffold.

12. The implantable medical structure of claim 10, for use in one or more of repair, treatment, regeneration, and augmentation of soft tissue and/or bone.

13. A cell culture substrate comprising the foam material of claim 1.

14. The foam material of claim 1, wherein:
the collagenous beads have a random shape.

15. A method for preparing a foam material, comprising:
freezing a plurality of collagenous beads at a selected temperature; and
subjecting the plurality of collagenous beads to freeze-drying, such that adjacent collagenous beads are fused together by collagen fibers;
wherein a foam material having channels between individual collagenous beads and/or channels between groups of collagenous beads is prepared;
wherein the foam material retains a 3-D shape.

16. The method of claim 15, comprising freezing the plurality of collagenous beads in a mould.

17. The method of claim 15, wherein a first foam material is prepared, the method further comprising forming at least a second foam material layer over the first foam material by:
(i) covering the first foam material with a second plurality of collagenous beads; and
(ii) subjecting the collagenous beads to freezing and freeze-drying; and
optionally repeating (i) and (ii) one or more times;
wherein a layered foam material is prepared.

18. The method of claim 17, further comprising:
(a) preparing at least the first and second foam materials;
(b) disposing one or more of one or more of cells, cell-seeded foam, and cell-seeded beads between the at least first and second foam materials;
wherein the cells aggregate the foam materials together to form a layered foam material.

19. The method of claim 17, wherein:
the collagenous beads of the first foam material or of at least one layer of foam material have a different shape or combination of shapes than the collagenous beads of at least one other layer of foam material.

20. The method of claim 15, comprising:
combining at least one chemical/biological agent, at least one additive, or at least one chemical /biological agent and at least one additive with the collagenous beads.

21. The method of claim 20, wherein:
the at least one chemical/biological agent is a cell, DNA, RNA, protein, an antibody or other binding protein, a drug, a growth factor, a hormone, an analgesic, or an anaesthetic, or a combination thereof.

22. The method of claim 20, wherein:
the at least one additive is a natural polymer, a biodegradable synthetic polymer, a non-biodegradable synthetic polymer, or a combination thereof.

* * * * *